(12) United States Patent
Zhang et al.

(10) Patent No.: US 10,561,392 B2
(45) Date of Patent: Feb. 18, 2020

(54) OPTICAL INTERFEROMETRIC SCANNING DETECTOR FOR CARDIOVASCULAR FUNCTION MONITORING

(71) Applicant: OmniSensing Photonics, LLC, Columbia, MD (US)

(72) Inventors: Jin Zhang, Ellicott City, MD (US); Shan Zhong, Clarksville, MD (US); Wei Chen, Ellicott City, MD (US); Zhonghua Zhu, Clarksville, MD (US); Lei Wu, Pleasanton, CA (US)

(*) Notice: Subject to any disclaimer, the term of this patent is extended or adjusted under 35 U.S.C. 154(b) by 348 days.

(21) Appl. No.: 15/403,184

(22) Filed: Jan. 11, 2017

(65) Prior Publication Data
US 2018/0192898 A1 Jul. 12, 2018

(51) Int. Cl.
*A61B 5/024* (2006.01)
*A61B 5/00* (2006.01)
*A61B 5/021* (2006.01)
*A61B 7/04* (2006.01)

(52) U.S. Cl.
CPC .............. *A61B 7/04* (2013.01); *A61B 5/0022* (2013.01); *A61B 5/02108* (2013.01)

(58) Field of Classification Search
None
See application file for complete search history.

(56) References Cited

U.S. PATENT DOCUMENTS

| 8,177,721 | B2* | 5/2012 | Antonelli | A61B 5/021 367/199 |
| 9,357,933 | B2* | 6/2016 | Baldwin | A61B 5/0059 |
| 10,206,576 | B2* | 2/2019 | Shcherbakov | A61B 5/0059 |
| 2018/0168453 | A1* | 6/2018 | Leizerson | A61B 7/00 |

* cited by examiner

*Primary Examiner* — Brian T Gedeon

(57) ABSTRACT

The object of the present invention is to disclose a novel optical miniaturized handheld medical device for convenient monitoring and/or data collection of detailed signals on human cardiovascular function. The implementation consists of a number of advanced technologies, including interferometric detection, phase controlled focusing beam steering, auto-tracking scheme and algorism, and integrated optical chip assembly to enhance the device's performance and miniaturization. Briefly, this handheld medical device directs a single or dual output laser beam(s) onto certain skin surface to detect the surface vibration velocity at the point where the laser hits the surface. The skin surface vibrates in response to cardiovascular signals, such as blood pressure pulses, turbulent blood flow through narrowed arteries, pumping actions of the heart, or the closure of the heart valves etc. The miniaturized apparatus thus is capable of detecting these signals for the assessment of cardiovascular functions in both healthy and disease conditions.

6 Claims, 4 Drawing Sheets

OPTICAL INTERFEROMETRIC SCANNING DETECTOR FOR CARDIOVASCULAR FUNCTION MONITORING

CROSS-REFERENCE TO RELATED APPLICATIONS

The present non-provisional application is a continuation-in-part of U.S. Non-Provisional patent application Ser. No. 15/146,354, filed May 4, 2016, entitled "Interferometric focusing beam optical cardiovascular sensor", which claims priority and other benefit from U.S. Provisional Patent Application Ser. No. 62/174,624, filed Jun. 12, 2015, and of U.S. Non-Provisional patent application Ser. No. 15/235,656, filed Aug. 11, 2016, entitled "1D laser beam guiding and tracking system and method for interferometric focusing beam optical cardiovascular sensor".

BACKGROUND OF THE INVENTION

The present invention relates generally to a portable apparatus that is designed as a miniaturized handheld device for cardiovascular function monitoring that can be used in either hospital or household. More specifically, the cardiovascular function monitor presented here is capable of detecting movements of skin surface due to the contraction(s) of the heart or blood vessels; or to turbulent blood flow through the heart or the blood vessels. The implementation of such portable equipment is based on a non-invasive method using optical interferometric laser scanning beam as the probing signal published in U.S. patent application Ser. No. 15/146,354, filed May 4, 2016, entitled "Interferometric focusing beam optical cardiovascular sensor".

Detection and monitoring of the activities of the heart or the blood vessels provide important physiological and pathological information on the cardiovascular system function of human body. Pumping action of the heart produces beats and closing of heart valves produces sounds, movement of the arteries contributes to the propagating pulses and turbulent blood flow through narrowed arteries produces arterial bruit [e.g., the blowing/swishing sound in a stenosed (narrowed) carotid artery] and so on. These cardiovascular signals which reflect functions of the Circulatory (Cardiovascular) System can be assessed by modern techniques, such as ultrasound-visualization, electro-cardiography (ECG), or auscultation with a stethoscope etc. However, none of these methods provides complete information on both the heart and the blood vessels. Also, there are numerous situations under which ordinary techniques are hampered, e.g., the heart sound(s) collected using an ordinary stethoscope is (are) faint or not even audible as the result of ambient noises. Furthermore, as cardiovascular diseases need early detection of the risks, none of these methods provides early enough diagnosis unless severe events bring the patients to the hospital. Therefore, it is the broad object of the present invention to provide a novel portable optical scanning detection system, wherein and whereby, cardiovascular signals as a result of the contractions of the heart or blood vessels, or turbulent blood flow through the heart chambers, valves, or blood vessels, could be detected and quantified, such that abnormalities, if any, of the cardiovascular function could be identified, quantitatively, at early-stage.

The following U.S. patents describe various prior art systems related to the above discussed problems but do not satisfy the long felt but unsolved need for portable, miniaturized multi-functional device that can perform multiple detection schemes at a minimum cost level:

U.S. Pat. No. 7,024,001, issued Apr. 4, 2006, to Tsutomu Nakada, Tokyo, discloses a laser based stethoscope that a radiation/light-receiving fiber, serving as a probe part for noninvasively irradiating with near-infrared light, is applied to the diseased part so as to measure, e.g., a change of the cerebral circulation blood flow. In this design, three semiconductor laser light sources with wavelengths $\lambda=760$, 800, 830 nm are used and applied to the diseased part, the reflection data from the diseased part is processed by a control device. The doctor can then "make a diagnosis with the doctor's ears by hearing with a receiver the change as the change of the frequency of the sound the pitch and volume of which are constant." This invention helps the detection on blood flow turbulence, but lacks solution on detecting other vital cardiovascular events, such as heart beat, heart sound, pulse wave, etc.

U.S. Pat. No. 7,128,714, issued Oct. 31, 2006, which proposes a non-contact method and an apparatus for continuously monitoring a physiological event in human or animals, namely blood pressure, involves utilizing a laser-based interferometer system to produce a waveform that is representative of continuous blood pressure in a subject. The invention utilizes a laser Doppler vibrometer which is substantially perpendicular to a skin surface of the subject wherein the skin surface is moveable in response to blood pressure. The principle and implementation of the invention is novel though its size, cost and applications are limited due to the traditional laser Doppler vibrometers.

BRIEF SUMMARY OF THE INVENTION

The present patent application disclosed here provides the most comprehensive cardiovascular function monitoring and meets portable device criteria in terms of size and cost.

The disclosed portable apparatus consists of three major parts: 1) An optical interferometric scanning sensor chipset; 2) A control and data processing unit; and 3) A communication unit.

In an exemplary embodiment, the optical interferometric scanning sensor chipset of the apparatus is manufactured with integrated photonics technology, with multiple functional units integrated on a single chip:

Laser source, which generates the $1^{st}$ laser light and makes the laser light be coupled into optical waveguide;

Tap coupler, which receives the $1^{st}$ laser light and splits it into the $2^{nd}$ laser light and reference laser light;

Light emitting part, which receives the $2^{nd}$ laser light and forms the $3^{rd}$ laser light that shines on the targeted scanning skin surface. It could have two different hardware implementations to achieve 1D laser beam scanning, either 1D angle scanning or 1D position scanning;

Light receiving part, which receives the reflected light (the $4^{th}$ laser light) from the targeted skin surface and forms the $5^{th}$ laser light. The light receiving part has the similar hardware implementation as the light emitting part that has the capability to do laser beam scanning, either 1D angle scanning or 1D position scanning.

2×4 interferometric mixer, which receives the $5^{th}$ laser light and reference light, and generates the beating signals as the $6^{th}$ laser light.

Balanced detector, which receives the $6^{th}$ laser light and converts the $6^{th}$ laser light into analog electrical signals. The received analog electrical signals are then amplified by TIAs and converted into digital signals by ADCs. Through DSP, the magnitude and phase of the cardiovascular signals can be recovered.

In an exemplary embodiment, the control and data processing unit performs the general control of optical interferometric scanning sensor chipset as well as the steering/switching and tracking algorithm for both emitting and receiving laser beams. It also does the preliminary data processing before sending the data out to either nearby paired smart devices (phones, tablets etc.) or the clouds.

In an exemplary embodiment, the communication unit is responsible for communicating with nearby paired smart devices (phones, tablets etc.) or clouds, through wireless technology, such as BLE, Wi-Fi, or LTE.

The interferometric sensing chipset is based on an integrated optical waveguide platform with built-in hybrid-packaged laser source and I/Q balanced receivers. A laser beam guiding and tracking scheme is also implemented to improve the tolerance to position shift due to human body movement during measurements. Thus, it has sensitivity advantages over other methods as well as size and cost.

BRIEF DESCRIPTION OF THE DRAWINGS

The present invention is illustrated and described herein with reference to the various drawings of exemplary embodiments, in which like reference numbers are used to denote like system components/method steps, as appropriate.

DETAILED DESCRIPTION OF THE INVENTION

Consistent with the inventions of "Interferometric focusing beam optical cardiovascular sensor", U.S. patent application Ser. No. 15/146,354 and "1D laser beam guiding and tracking system and method for interferometric focusing beam optical cardiovascular sensor", U.S. patent application Ser. No. 15/235,656, this invention describes the implementation of a miniaturized handheld medical device for the cardiovascular signals monitoring purpose.

Figure 1:
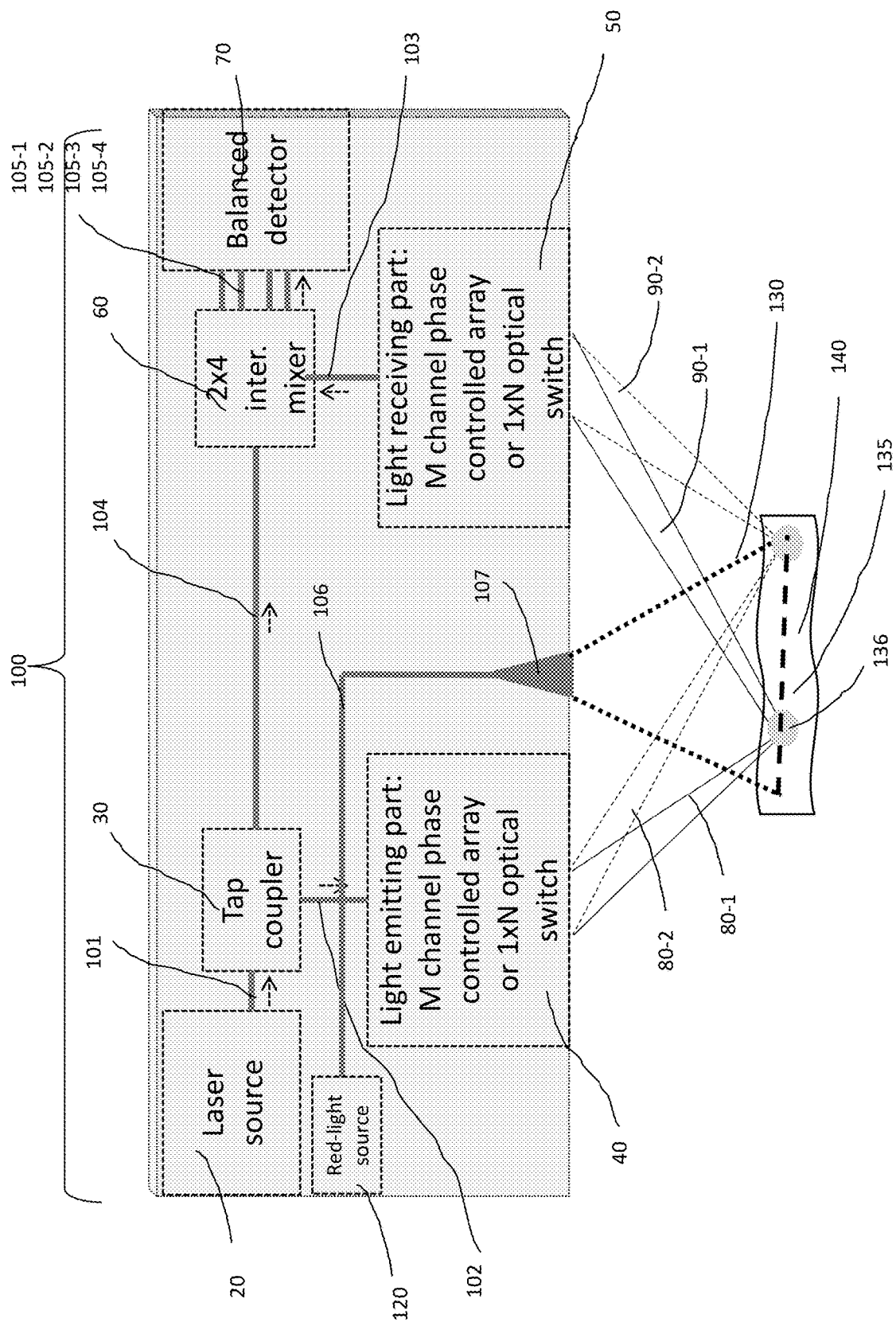
FIG. 1 is a schematic diagram of the design for the integrated optical scanning sensor chipset with multiple functions, such as Interferometric focusing beam steering, I/Q balanced detection, etc., for the purpose of detection and monitoring of the cardiovascular signals.

Referring to FIG. 1, this is an integrated optical waveguide chipset 100 that consists of 6 major functional parts: the laser source 20, the tap coupler 30, the light emitting part 40, the light receiving part 50, the 2×4 interferometric mixer 60 and the 2-pair balanced detectors 70. On the optical chip, laser source 20 generates the $1^{st}$ laser 101. The tap coupler 30 receives the $1^{st}$ laser and splits it into the $2^{nd}$ laser 102 and the reference light 104. The $2^{nd}$ laser 102 is received by the light emitting part 40 and converted into the $3^{rd}$ laser 80, where the $3^{rd}$ laser can shine on the targeted scanning skin surface 140 at controllable output angle or output position. Its phase is constant but the amplitude can be dithered as a function of time t for laser beam guiding and tracking purpose. The diffused reflection light from the targeted scanning surface 140, the $4^{th}$ laser light 90, has an angle dependent distribution. At the targeted scanning skin surface 140, the phase of $4^{th}$ laser light 90 is modulated by local cardiovascular event(s). Only a portion of the $4^{th}$ laser light 90 with optimized reflection angle or position can be received or collected by light receiving part 50. The light receiving part 50 converts the $4^{th}$ laser light 90 into the $5^{th}$ laser light 103. The $5^{th}$ laser light 103 is mixed with the reference light 104 inside the 2×4 interferometric mixer 60, generating the $6^{th}$ laser light 105, which contains a set of optical beating signals +I/−I 105-1, 105-2, +Q/−Q 105-3, 105-4. In balanced detectors 70, the $6^{th}$ laser light 105 is converted into electrical signals.

As an option, the visible red-color light source 120 generates the $1^{st}$ red-color light 106. The slab waveguide 107 receives the $1^{st}$ red-color light 106 and shines it onto the targeted scanning skin surface 140, forming a visible 1D linear marker on the targeted skin surface 140.

Figure 2:
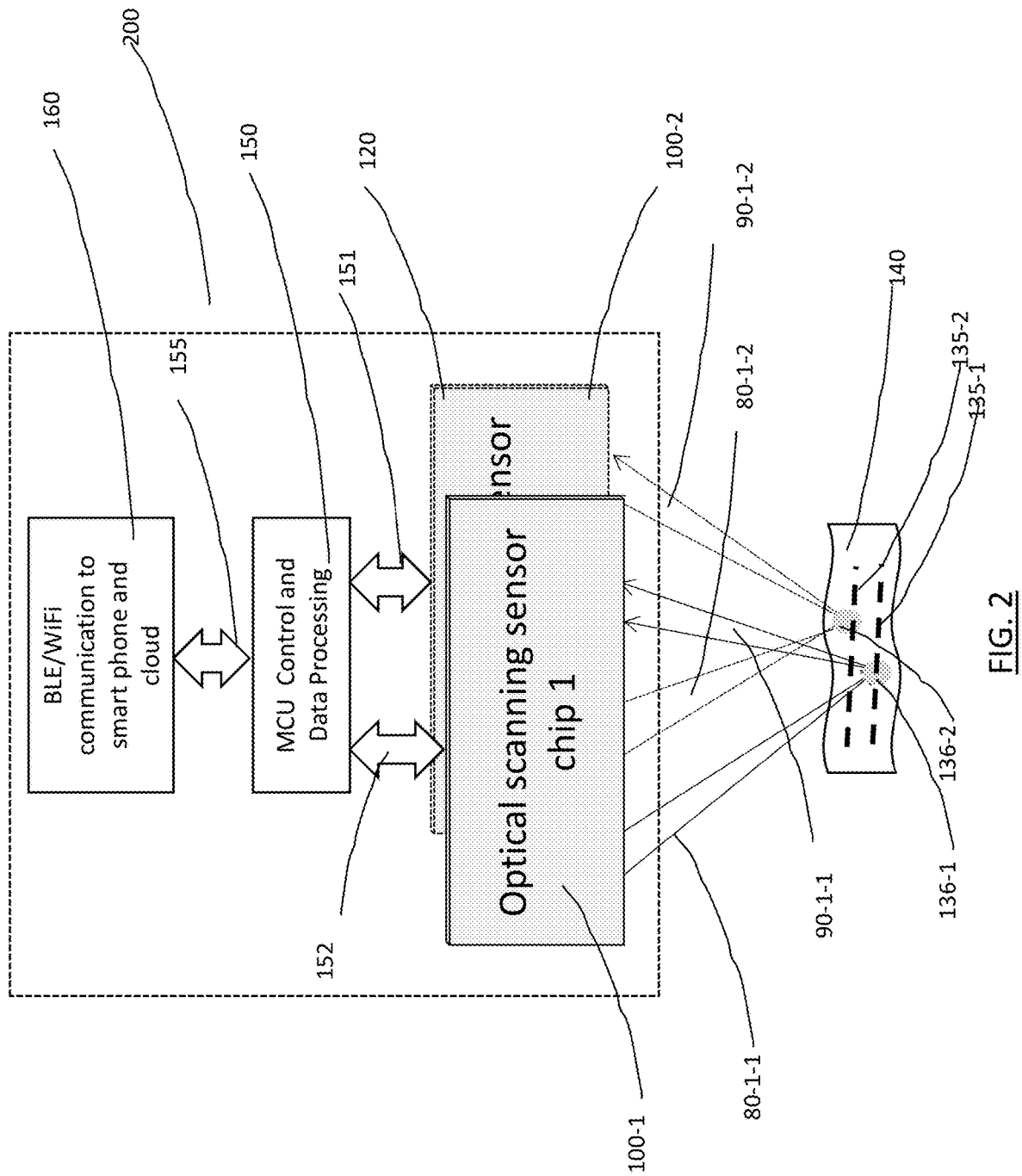
FIG. 2 is a schematic diagram of an exemplary implementation of the miniaturized device comprising of three major parts for convenient cardiovascular signals monitoring.

The system diagram of the proposed miniaturized medical device for cardiovascular signals monitoring can be found in FIG. 2. The miniaturized device 200 consists of three major parts: 1) Two optical scanning sensor chipsets 100-1 and 100-2, each to detect a linear targeted skin surface with distance about 1.5-2 cm. In combination, they work together to collect timing sensitive waveforms for key parameters calculation, such as local pulse wave velocity (PWV). Normally, these two optical scanning sensors are integrated into one chipset; 2) The control and data processing unit 150, performs the general control of optical interferometric scanning sensor chipset as well as the steering/switching and tracking algorithm for both emitting and receiving laser beams. It also does preliminary data processing before sending the data out to either nearby paired smart devices (phones, tablets etc.) or the clouds; 3) The communication unit 160 is responsible for the communication between the miniaturized medical device and nearby paired smart devices (phone, tablet etc.) or remote clouds through BLE, Wi-Fi or LTE.

Figure 3:
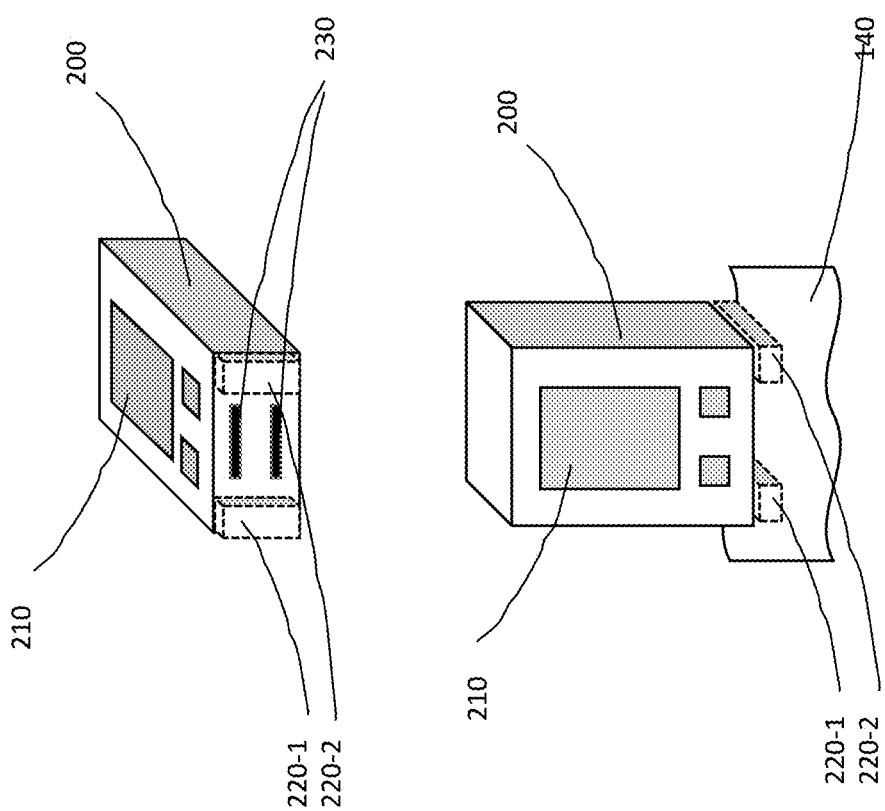
FIG. 3 is a conceptual drawing illustrating the possible mechanical design of the miniaturized device with two optical scanning sensors implemented.

Referring to FIG. 3, the conceptual design of the miniaturized medical device 200 could be a palm size rectangular prism. At the bottom end, there are two open slots 230 serving as open windows for two scanning laser beams, which are bout 1.5-2 cm apart. It may also have two supporting structures 220-1 and 220-2 with suitable materials as the buffer between the miniaturized medical device 200 and the target scanning skin surface 140. On the front side, it may have one LCD display and few buttons 210 for device control and communication purpose.

Figure 4:
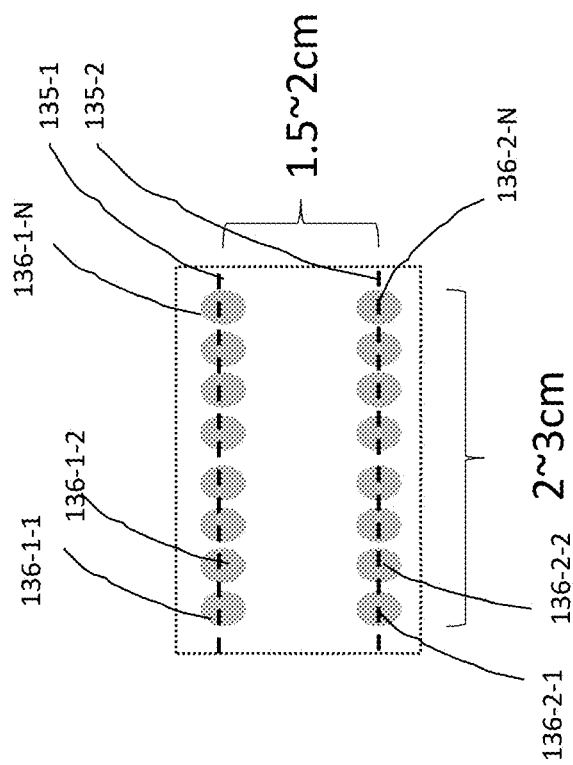
FIG. 4 is a schematic diagram of the scanning zone and location of the optical scanning beam on the targeted scanning skin surface.

Referring to FIG. 4, with two built-in optical scanning sensors 100-1 and 100-2, the miniaturized device 200 can perform laser beam steering and scanning along the two separate lines, marked by visible red-color lights 135-1 and 135-2. As the emitting laser beam 80 of each optical scanning chipset can be steered or switched to N directions in 1D, the device can scan multiple spots 136-1-1, 136-1-2, ... 136-1-N, and 136-2-1, 136-2-2, ... 136-2-N, simultaneously, on the targeted scanning skin surface.

Figure 5:
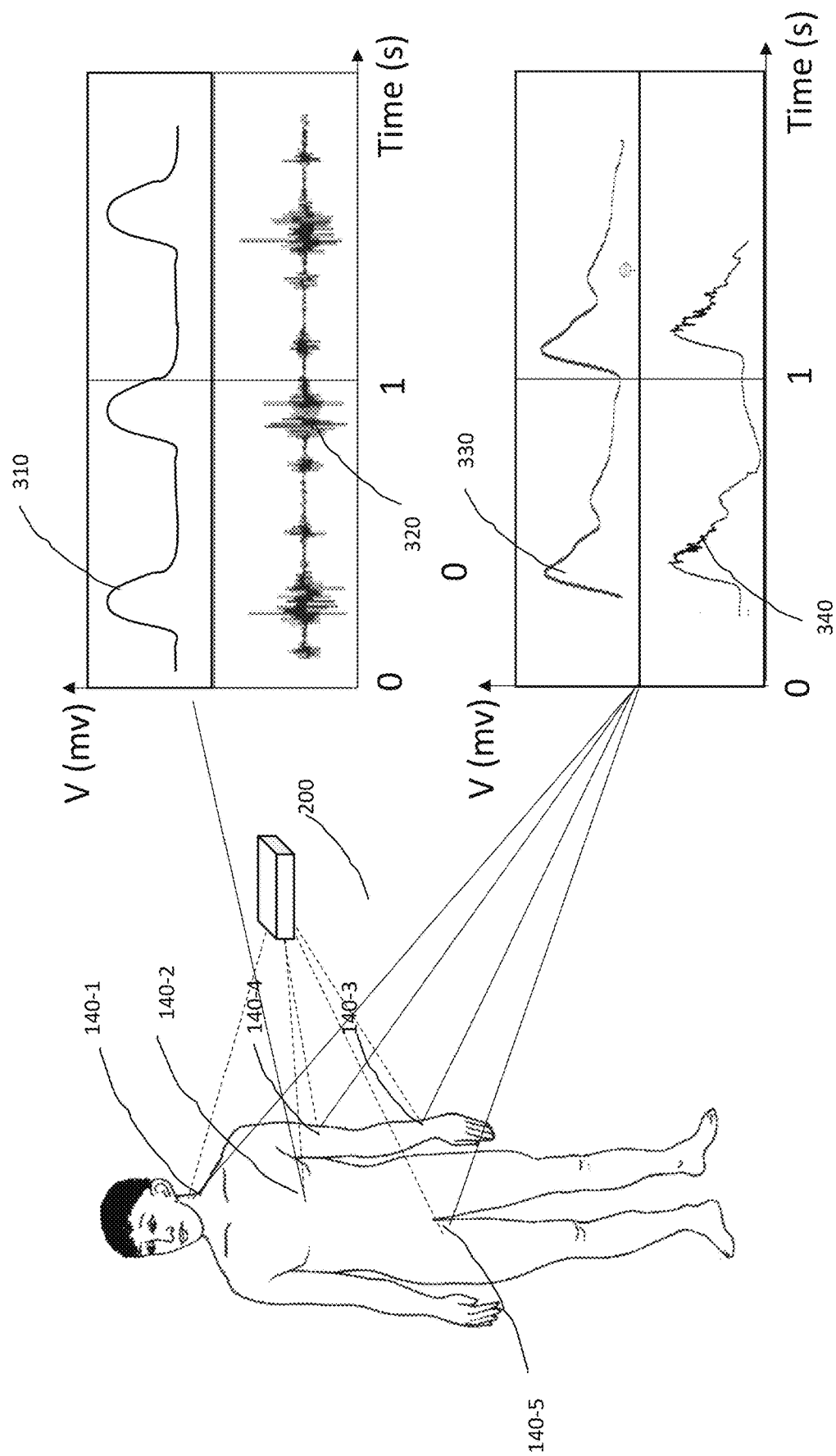
FIG. 5 is a schematic diagram of the potential areas of human body to which the miniaturized device can be applied and exemplary signals at the chest wall (for heart) or at certain skin surfaces (for blood vessels).

Referring to FIG. 5, it illustrates that this miniaturized device 200 can be attached to multiple areas of human body for different detecting purposes, such as 1) the neck (for carotid artery); 2) forearm (for brachial artery) or wrist (for radial artery); 3) leg (for femoral artery) or ankle (for dorsalis pedis artery); or 4) the chest or thorax (for the heart). At the chest, the apparatus could detect the skin movement 310 due to the pumping action of the heart or 320 to the closing of the heart valves (heart sounds). Whereas at the neck or the extremities, the apparatus detects the skin movement 330 due to pressure-related artery displacement resulting in pulsating waveforms or 340 to turbulent blood flow through stenosed (narrowed) arteries, wherein the extent and accurate position of the stenosis can be calculated and located.

What is claimed is:

1. An apparatus for cardiovascular function monitoring, comprising:
    a miniaturized rectangular prism having at its bottom side two slots for passing two scanning laser beams and two visible light beams to two targeted skin surfaces on an area of a human body, wherein the two visible light beams form on the two targeted skin surfaces two respective visible linear markers that are separated with a predefined distance, and wherein the two scanning laser beams are steered and scan at multiple spots along the two respective visible linear markers simultaneously;
    two optical scanning sensor chipsets received within the miniaturized rectangular prism, and configured to detect two respective diffused laser beams reflected from the two linear targeted skin surfaces, wherein phases of the two diffused laser beams are modulated by local cardiovascular events within the area of the human body;
    a control and data processing unit configured to control the two optical scanning sensor chipsets and process detection data of the two optical scanning sensor chipsets; and
    a communication unit configured to communicate with nearby paired smart devices or remote clouds for further processing of the detection data.

2. The apparatus or method of claim 1, wherein the two optical scanning sensor chipsets each comprises:
    a laser source configured to generate a first laser;
    a tap coupler configured to split the first laser into a second laser and a reference light;
    a light emitting part configured to convert the second laser into a third laser and direct the third laser to a corresponding linear targeted skin surface of the two linear targeted skin surfaces;
    a light receiving part configured to receive a fourth laser reflected from the corresponding linear targeted skin surface and convert the fourth laser into a fifth laser, wherein the fourth laser is modulated by a vibration on the corresponding linear targeted skin due to local cardiovascular events;
    an interferometric mixer configured to mix the fifth laser with the reference light to generate a sixth laser; and
    a balanced detector configured to convert the sixth laser into electrical signals.

3. The apparatus of claim 2, wherein the two optical scanning sensor chipsets each further comprises:
    a red-color light source configured to generate one of the two visible light beams; and
    a slab waveguide configured to receive the visible light beam and shine the visible light beam onto the corresponding linear targeted skin surface to form the visible linear marker.

4. The apparatus of claim 1, wherein the area of human body comprises at least one of the following: neck, forearm, leg, and chest.

5. The apparatus of claim 1, wherein the predefined distance is 1.5-2 cm.

6. The apparatus of claim 1, wherein said communication unit is configured to communicate with the nearby paired smart devices and the remote clouds through wireless technology.

* * * * *